United States Patent [19]

Leach

[11] 4,050,311

[45] Sept. 27, 1977

[54] SPHYGMOMANOMETER

[76] Inventor: John Meredith Leach, Box 341, Port Jefferson, N.Y. 11777

[21] Appl. No.: 651,207

[22] Filed: Jan. 21, 1976

[51] Int. Cl.$^2$ ............................................. G01L 19/00
[52] U.S. Cl. ................................. 73/389; 128/2.05 G
[58] Field of Search ................................. 73/389, 402; 128/2.05 G, 2.05 N, 145.7

[56] References Cited

U.S. PATENT DOCUMENTS

| 3,738,357 | 6/1973 | Hayes | 128/2.05 G |
| 3,828,811 | 8/1974 | Natkanski | 128/2.05 G |
| 3,906,939 | 9/1975 | Aronson | 128/2.05 G |

Primary Examiner—Donald O. Woodiel

[57] ABSTRACT

A hand held all-visibility (no stethoscope required) blood pressure measuring instrument comprising a manifold, a combination blood pressure and systolic-diastolic points indicating direct reading gauge physically and funtionally connected to the manifold, a squeeze bulb physically and functionally connected to the manifold and forming the hand grip for holding the instrument and having a stiffening member connected to the manifold and extending through the interior of the bulb to prevent bending distortion of the bulb and resultant waver of the gauge, and a short stroke, quick action press type air release valve physically and functionally connected to the manifold in a position where it can be completely operated solely by very short strokes of the thumb of the holding hand (either right or left) while the hand is in a completely normal position and the gauge is in a fully readable position while being held steady and still.

10 Claims, 4 Drawing Figures

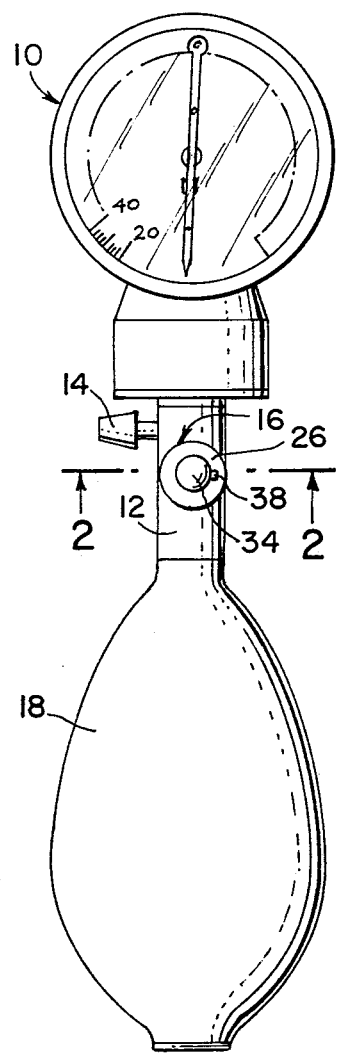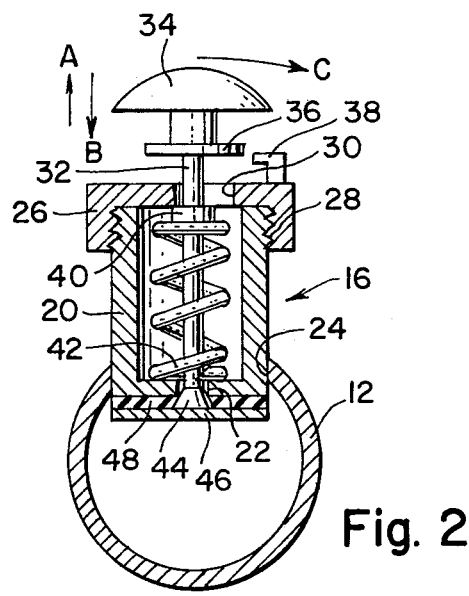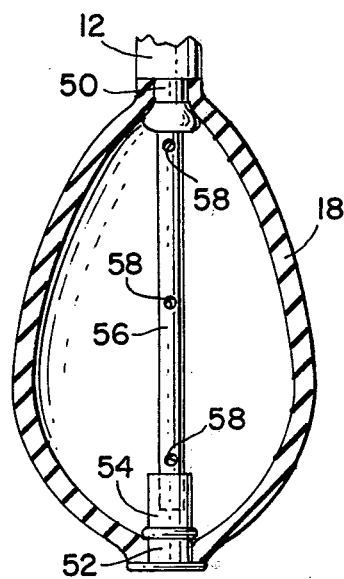
Fig. 1
Fig. 2
Fig. 3

SPHYGMOMANOMETER

BACKGROUND OF THE INVENTION

Since the beginning of the use of mechanical gauges instead of mercury manometers in sphygmomanometers the relatively small mechanical gauge has presented a problem in holding during the blood pressure measuring operation. It either had to be held in one of the operator's hands, thereby preventing that hand from being used for any other purpose, or laid on some nearby object which made it vulnerable to being pulled or knocked off onto the floor and being ruined. It was tried hanging it onto the cuff on the patient's arm but this made it hard for the operator to see to read and was also vulnerable to falling off onto the floor and could be read by the patient which was many times not desirable.

This holding problem was in part solved by equipment such as that disclosed by U.S. Pat. No. 2,934,061 in which the gauge is mounted on the air release valve casing in that the holding of the gauge was improved but other undesirable conditions were created. For example, this type of mounting caused the gauge to waver and vibrate when the bulb was squeezed or the screw type air release valve was opened or closed and this was true even though a handle was placed along side of the bulb in an effort to steady the gauge because the handle interferred with the squeezing of the bulb because the bulb could only be squeezed on one side which caused it to buckle and waver the gauge. Also, the screw type valve had to be operated by the thumb and the forefinger which meant that both of these fingers had to be substantially moved from their natural position when holding the instrument to positions where they could grasp and turn the screw valve which again wavered the gauge very noticeably and made it difficult to read. These disturbing factors were particularly aggravating because the gauge is always read during the deflation phase of the measuring operation when the release valve is frequently opened and closed several times because the heart beat is at times hard to hear in a stethoscope so that the valve has to be closed and the bulb squeezed to raise the pressure reading and the valve again opened to permit the pressure reading to drop slowly and check the point where the heart beat sound stopped.

Also, a left handed person could not use a right handed instrument and vice versa so that both types had to be available which is costly and time wasting.

SUMMARY OF THE INVENTION

The present invention is a hand held sphygmomanometer wherein the gauge, squeeze bulb and air release valve are all mounted on a common manifold and yet the bulb can be squeezed and the air release valve operated without disturbing the stability of the gauge at any time even very slightly. This is made possible because a stiffener rod or tube is rigidly connected to the manifold and extends down through the interior of the bulb and is fastened to the free end of the bulb on the inside so that the bulb can not flex, bend or otherwise move relative to the gauge which is also rigidly connected to the manifold. The bulb can be freely squeezed without restriction in any way by the stiffener rod which does not interfere with such squeezing.

Complete gauge stability is also made possible because the air release valve is a short stroke, quick action press type and is placed where it is directly under the thumb of the operator's hand holding the instrument so that it can be operated by the thumb without requiring any change of position of the thumb or any other finger of the holding hand with a very short stroke of the thumb which can be as small as one sixty-fourth of an inch which disturbs nothing at all including the gauge. The instrument of the present invention can be used with equal accuracy and comfort by either a right or left handed operator which greatly reduces the number of instruments required by a clinic, hospital or the like.

The instrument of the present invention is of great value when the gauge is of the all-visibility type wherein no stethoscope is required to note the systolic and diastolic points because they are both indicated on the gauge. In this type of instrument the operation is improved if the deflation phase is brought about by opening and closing the air release valve frequently instead of just permitting the valve to remain slightly open during all of the deflation phase. This is because the amplified oscillation of the gauge needle requires very slightly more time than a continuous movement of the needle.

The objects of the present invention are to provide advantages over conventional blood pressure measuring instruments as set forth above in this summary and elsewhere in this specification.

Other objects and advantages will be apparent to to those skilled in the art upon recourse to the following specification and claims.

BRIEF DESCRIPTION OF THE DRAWINGS

The now preferred embodiment of the present invention is disclosed in the accompanying drawings which is to be considered as descriptive and not limitative as many changes and modifications can be made in the structural details without departing from the spirit of the invention.

In the drawings:

FIG. 1 is a gauge face view of the measuring instrument of the present invention;

FIG. 2 is a cross sectional view of the short stroke quick action air release valve of the present invention;

FIG. 3 is a central sectional view of the bulb showing the bulb stiffener of the present invention.

Figure 4:
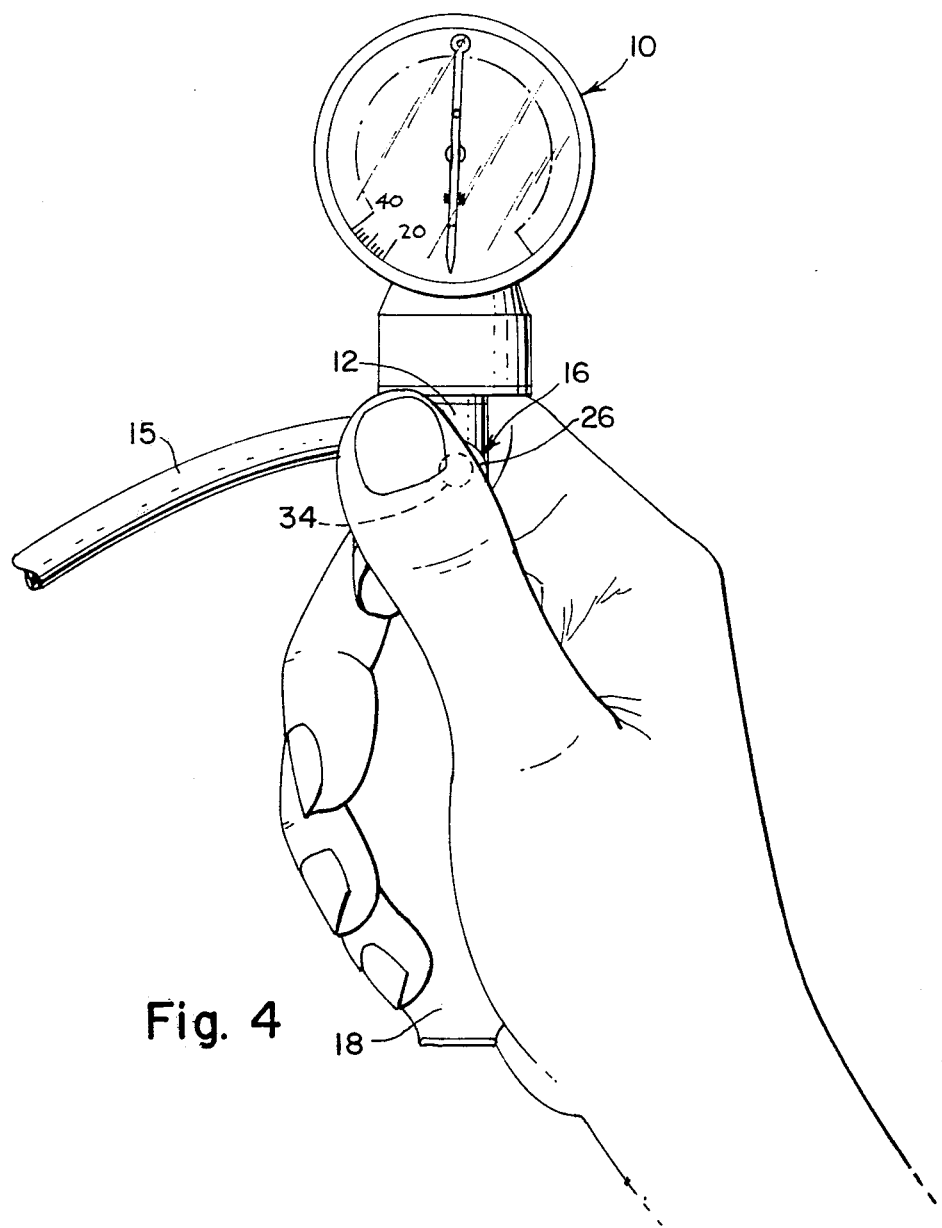
FIG. 4 is a view of the measuring instrument of the present invention showing how it is held in a hand of an operator.

The present invention comprises a gauge 10 which may be any desired type of pressure gauge although an aneroid bellows type is usually used on sphygmomanometers. Since such gauges are well known no details of this gauge will be described. The preferred type of gauge is that disclosed in U.S. patent application Ser. No. 628,227, filed Nov. 3, 1975. This is because the type of control valve to be later described works peculiarly well with that type of gauge, which requires no stethoscope.

A manifold 12 is suitably attached to the inlet connection for the gauge 10 as by screwing onto a threaded fitting normally present at that point. A fitting 14 extends from the manifold 12 and is adapted to receive and retain a tube 15 (see FIG. 4) for connection to a conventional live body contact cuff. A manually operable release valve 16 is also connected to the manifold 12 and will be described in detail later. An inflation bulb is attached at the opposite end of the manifold 12 as shown at 18. The valve 16 comprises a body 20 provided with an outlet orifice 22 and is suitably attached to the manifold 12 as by a pressure fit at the point 24. A top 26 is threaded onto the body 20 as shown at 28. An elongated opening 30 in the top 26 serves as an outlet for the discharged air. A valve stem 32 also projects through the opening 30. A press button 34 having a flange 36 is suitably attached as by threading onto the valve stem 32. A detent 38 is carried by the top 26 for coaction with the flange 36 as will be later described. A stop 40 is rigidly attached to the valve stem 32 and a compression spring 42 in confined about the valve stem 32 between the stop 40 and the bottom of the body 20 so as to urge the valve stem upwardly as viewed in FIG. 2. The valve stem 32 is formed with a tapered section 44 which coacts with the bottom edge of the orifice 22 to provide a closed valve when in the position shown in FIG. 2. A head 46 is suitably attached to the bottom of the tapered section 44 and carries suitably adherred to it a soft rubber, plastic or other desired material washer 48 which provides an added air seal around the valve seat when it is compressed against the junction of the orifice edge and the tapered section 44 and thus avoids all air leakage.

A combined valve and bulb retention ring 50 is suitably attached as by threading to the bottom of the manifold 12 so that the retention ring part will hold the bulb 18 in position on the bottom of the manifold as shown in FIG. 3. The valve consists of a conventional ball, disc, or slitted rubber tube type of well known construction and functions to let air pass from the bulb 18 when it is squeezed into the manifold and thence to the cuff and gauge but will not allow any return flow of the air into the bulb when it recovers from a squeeze. During the said recovery of the bulb 18 the air enters the bulb through a valve 52 at the opposite end of the bulb 18 but valve 52 does not allow any air to return out of the bulb during a squeeze of the bulb 18. In this manner the bulb 18 acts as an air pump during repeated squeezings and inflates the cuff to restrict the arterial blood flow by the cuff and also actuated the gage 10 to register the blood pressure. The valve 52 may be of the conventional ball, disc, or plug type which are well known articles of commerce.

A section of tubing 54 is suitably attached, as by soldering, to the upper end of the valve 52 and slidably receives one end of a tube 56 which is suitably attached, as by silver soldering, at the opposite end to the valve 50. The tube 56 is provided with any desired number of openings 58 which permit air to pass from the bulb 18 through valve 50 and into the manifold 12 and also permit air to pass from the outside through valve 52 into the bulb 18.

The telescoping tubes 54 and 56 act as a stiffener for the bulb 18 and because of their small cross-section do not interfere to any extent with squeezing of the bulb but do not transmit the squeezing movements to the gauge. Being as these tubes are rigidly connected to the manifold 12 and also to the lower end of the bulb 18 the weight of the gauge, manifold, valve and tubing connected to fitting 14 can not cause these elements to sag relative to the bulb 18 and cause the gauge 10 to waver or vibrate and interfere with the reading of the gauge.

Because the valve 16 is in a position always underlying the thumb on the hand of the operator holding the instrument it is never necessary to change the position of the thumb to operate the valve to either close or open it, as shown in FIG. 4. The movement of the thumb to open or close the valve 16 is approximately one sixty-fourth of an inch, which minute movement to no extent disturbs the gauge or requires any significant effort on the part of the operator.

Whenever a blood pressure measurement has been completed and it is desired to let any remaining air drain from the cuff, the valve buttom is pushed all the way in the direction of the arrow B and then rocked to one side in the direction of arrow C unti the flange 36 catches under the detent 38 where it will be held to permit the escape of air from the cuff as it is being removed from the patient's arm. When the flange is pushed lightly away from the detent and released it will move in the direction of arrow A to valve closed position.

Although the tapered section 44 maintains an air-tight seal with the edge of the orifice 22 under the force of the spring 42 only a very small movement to open the valve enough to allow release of air by the tapered section. This movement can be as small as one sixty-fourth of an inch or even smaller if an operator is capable of moving his thumb a shorter distance than that. The operation of the sphygmomanometer of the present invention is basically the same as the usual operation of a conventional instrument except that the features of the present invention enable it to be operated more comfortably and accurately as above explained. When an all-visibility (no stethoscope required) type gauge is used, the frequent closing and opening of the valve 16 during the deflation phase of the cuff as above described is greatly facilitated by the short stroke, fast action valve 16 in which opening or closing requires almost no effort and causes absolutely no gauge waver.

The foregoing is to be considered as descriptive and not limitative as many changes and modifications can be made therein without departing from the concept of the invention.

The invention having been described, what is claimed is:

1. A rigidly structured, functionally stable, manually hand held measuring instrument comprising a manifold, a gauge directly and rigidly mounted on and functionally connected to said manifold, a squeeze bulb also directly and rigidly mounted on and functionally connected to said manifold, and a short stroke, quick action press type air escape valve also directly and rigidly mounted on and functionally connected to said manifold at a position where it can be freely operated to permit air escape or stop air escape instantly at the will of the operator by a very slight up or down but no extending, contracting nor sidewise movement of the operator's thumb on one hand(either right or left) alone so as to leave the other four fingers of the same hand free to securely and motionlessly support the instrument by said bulb and at the same time also squeeze or release the bulb while the operating hand and the thumb and all four fingers thereon are in a completely natural position so that no movement of the instrument in any direction is caused thereby, and also the said gauge is in a perfect and natural, unobstructed viewing position by said operator whose other hand is left entirely free constantly throughout a measuring operation.

2. A manually hand held measuring instrument as specified in claim 1 which is a blood pressure measuring instrument.

3. A manually hand held measuring instrument as specified in claim 1 in which a stiffening member extends through the interior of said bulb and is connected at one end to said manifold and at the opposite end to said bulb.

4. A manually hand held measuring instrument as specified in claim 3 in which said short stroke, quick action press type air release valve includes a press button which can be moved to one side when in fully depressed valve open position and a detent under which said press button catches when so moved sidewise to hold said valve in depressed valve open position.

5. A manually held measuring instrument as specified in claim 3 in which said gauge is an all-visibility combination blood pressure and systolic-diastolic points indicating direct reading type.

6. A manually hand held measuring instrument as specified in claim 1 in which said short stroke, quick action press type air release valve includes a press button which can be moved to one side when in fully depressed valve open position and a detent under which said press button catches when so moved sidewise to hold said valve in depressed valve open position.

7. A manually hand held measuring instrument as specified in claim 1 in which said gauge is an all visibility combination blood pressure and systolic-diastolic points indicating direct reading type.

8. A manually hand held measuring instrument comprising a manifold, a gauge mounted on and functionally connected to said manifold, a squeeze bulb mounted on and functionally connected to said manifold, and a stiffening and stabilizing member rigidly connected to said manifold and extending through the interior of said squeeze bulb so as not to interfere with the squeezing thereof and in contact with the otherwise free end of said bulb to prevent it from distorting or bending under the weight of said manifold and gauge or bulb squeezing or other operations so as to prevent any wavering or vibrating of said gauge at any time.

9. A manually hand held measuring instrument as specified in claim 2 which further includes an air release valve also mounted on said manifold.

10. A manually hand held measuring instrument as specified in claim 2 in which said gauge is an all-visibility combination blood pressure and systolic-diastolic points indicating direct reading type.

* * * * *

Disclaimer

4,050,311.—*John Meredith Leach,* Port Jefferson-Belle Terre, N.Y. SPHYGMO-
MANOMETER. Patent dated Sept. 27, 1977. Disclaimer filed Nov. 23,
1981, by the inventor.

Hereby enters this disclaimer to claims 1, 2 and 9 of said patent.
[*Official Gazette Feb. 2, 1982.*]